United States Patent [19]

Theodoridis

[11] Patent Number: 4,885,025

[45] Date of Patent: Dec. 5, 1989

[54] HERBICIDAL TETRAZOLINONES AND USE THEREOF

[75] Inventor: George Theodoridis, Princeton, N.J.

[73] Assignee: FMC Corporation, Philadelphia, Pa.

[21] Appl. No.: 945,925

[22] Filed: Dec. 23, 1986

[51] Int. Cl.$^4$ ................. C07D 257/04; A01N 43/713
[52] U.S. Cl. ......................................... 71/92; 548/251
[58] Field of Search ............................. 548/251; 71/92

[56] References Cited

U.S. PATENT DOCUMENTS

| | | | |
|---|---|---|---|
| 3,954,442 | 5/1976 | Becker et al. | 71/108 |
| 4,292,070 | 9/1981 | Wakabayashi et al. | 71/96 |
| 4,426,220 | 1/1984 | Parg et al. | 71/98 |
| 4,490,165 | 12/1984 | Spatz et al. | 71/88 |
| 4,514,210 | 4/1985 | Aya et al. | 71/92 |
| 4,550,192 | 10/1985 | Rogers et al. | 560/62 |
| 4,618,365 | 10/1986 | Covey et al. | 71/92 |

FOREIGN PATENT DOCUMENTS 160447 of 1983 German Democratic Rep. .
WO85/01939 5/1985 PCT Int'l Appl. .

*Primary Examiner*—David B. Springer
*Attorney, Agent, or Firm*—Robert M. Kennedy; H. Robinson Ertelt; Abner Sheffer

[57] ABSTRACT

Disclosed are herbicidal aryltetrazolinones in which the aryl moiety is a substituted-phenyl radical having at the 5-position of the phenyl ring a group of the formula

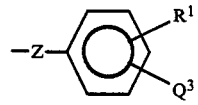

wherein Z is O, S, NH, or alkylamino; $R^1$ is H, alkyl, halogen, haloalkyl, $NO_2$, $NH_2$, CN, lower alkoxy or lower alkylthio; and $Q^3$ is a group of the formula $-[O-CH(R^{4a})CO]_m-OCH(R^4)Q^2$ in which $Q^2$ is $-C(O)R^3$ or $-CN$; $R^4$ and $R^{4a}$ are each independently H, $CH_3$ or $C_2H_5$; $R^3$ is OH, alkoxy, alkylthio, lower alkenyloxy or alkynyloxy, amino, arylamino, alkylamino, alkenylamino, alkynylamino, alkoxyamino or alkyl-, haloalkyl- or arylsulfonylamino of the formula $-NHSO_2R^5$ or $-N(SO_2R^5)SO_2R^6$, or an $-O-N=R^8$ radical where $R^8$ is alkylidene; $R^5$ and $R^6$ are each independently alkyl, haloalkyl or aryl; and "m" is zero or one.

13 Claims, No Drawings

HERBICIDAL TETRAZOLINONES AND USE THEREOF

This invention relates to novel herbicides for weed control in agriculture, horticulture and other fields where it is desired to control unwanted plant growth, such as grassy or broadleaf plant species. The information also relates to intermediates for the production of herbicides.

One aspect of this invention relates to herbicidal compounds of the formula

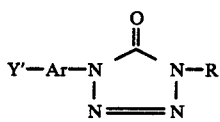

(Formula I)

where Y'—Ar— is a substituted phenyl radical (e.g. of the formula

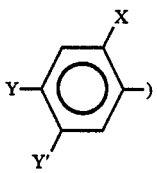

in which Y' is at the 5-position of Ar (i.e. meta to the nitrogen of said formula I) and Y' is

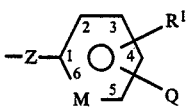

where Z may be O, S, NH or alkylamino (such as lower alkylamino, e.g. methylamino) and Q is

$Q^2$ is —C(O)$R^3$ or —CN.

M is CH or N.

$R^4$ and $R^{4a}$ may be H or $CH_3$ or $C_2H_5$ and $R^3$ may be OH, alkoxy (e.g. lower alkoxy such as methoxy or ethoxy) alkylthio (e.g. lower alkylthio such as thiomethyl), lower alkenyloxy or alkynyloxy (e.g. allyloxy or propargyloxy), amino, arylamino (e.g. phenylamino), alkylamino (e.g. lower alkylamino such as methylamino or dimethylamino), alkenylamino (e.g. diallylamino), alkynylamino (e.g. proparpylamine), alkoxyamino (e.g. lower alkoxyamino such as methoxyamino) or alkyl-, haloalkyl- or arylsulfonylamino of the formula —NHSO$_2R^5$ or —N(SO$_2R^5$)SO$_2R^6$, or an —O—N=$R^7$ radical where $R^7$ is alkylidene (e.g. lower alkylidene such as isopropylidene).

$R^5$ and $R^6$ may be independently alkyl (e.g. lower alkyl such as methyl, ethyl or propyl), haloalkyl (e.g. halo lower alkyl such as trifluoromethyl) or aryl such as phenyl or substituted phenyl, (e.g. alkoxy-substituted and/or halo-substituted phenyl).

"m" may be zero or 1.

R' may be H, alkyl (e.g. lower alkyl such as methyl), halogen such as Cl, Br or F, haloalkyl (e.g. lower haloalkyl such as $CF_3$, $CH_2F$ or $CHF_2$), nitro, $NH_2$, lower alkoxy or alkylthio (e.g. $OCH_3$ or $SCH_3$) or cyano.

There may be a plurality of R' substituents on the same benzene ring.

Z may be O, S, NH or alkylamino (such as lower alkylamino, e.g. methylamino).

In Formula I above, Ar and R are so chosen that when Y' is methoxy or propargyloxy (instead of having the formula given above) the compound is a herbicide. Compounds in which Y' in Formula I is methoxy or propargyloxy are, for convenience, here designated as the Methoxy Analogs and the Propargyloxy Analogs of the claimed novel compounds. Such Methoxy Analogs and Propargyloxy Analogs are well known in the art. For instance, the Propargyloxy Analog of Compounds 1, 2 and 8-10 of this application (see Table I below) is the compound 1-[4-chloro-2-fluoro-5-(2-propynyloxy)-phenyl]-4-(3-fluorophenyl)-5H-tetrazol-5-one which is compound 121 of PCT International Application No. WO 85/01939 published May 9, 1985.

The substituent R on the tetrazolinone ring may, for instance, be any of those shown in the above-mentioned International Application No. WO 85/01939. For instance, R may be alkyl (preferably of 1 to 6 carbon atoms), haloalkyl (preferably of 1 to 5 carbon atoms), alkoxyalkyl (preferably of 2 to 6 carbon atoms), alkylthioalkyl (preferably of 2 to 6 carbon atoms), cyanoalkyl (preferably of 1 to 5 alkyl carbon atoms), haloalkoxyalkyl (preferably of 2 to 6 carbon atoms), trifluoromethylthio, alkenyl (preferably of 2 to 5 carbon atoms), or haloalkenyl (preferably of 2 to 5 carbon atoms).

Preferably, "Ar" carries a substituent (i.e. other than H) at the 2-position or the 4-position of the phenyl radical, most preferably at both the 2- and 4-positions.

X may be H, halogen such as Cl, Br or F (preferably F), alkyl (e.g. lower alkyl such as methyl), haloalkyl (e.g. lower haloalkyl such as $CF_3$, $CH_2F$ or $CHF_2$) or nitro; and Y may be H, halogen such as Cl, Br or F (preferably Br or Cl), alkyl (e.g. lower alkyl such as methyl), alkoxy (e.g. lower alkoxy such as methoxy), haloalkyl (e.g. lower haloalkyl such as fluoroalkyl), —SOCF$_3$ or halo lower alkoxy such as —OCHF$_2$. Presently preferred X, Y substituents are: 2-F, 4-Cl; 2-F, 4-Br; 2,4-Cl; 2-Br, 4-Cl; and 2F, 4-CF$_3$.

A broader aspect of the invention relates to herbicidal compounds of the formula.

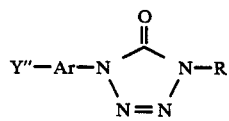

(Formula II)

where Y'" is at the 5-position (meta to the nitrogen directly attached to Ar) and Y'" is

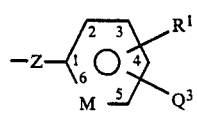

in which $Q^3$ may be Q or H, halogen (such as Cl, Br or F), alkyl (such as lower alkyl, e.g. methyl), haloalkyl (such as halo lower alkyl, e.g. $CF_3$, $CHF_2$, $C_2F_5$ or $CH_2F$), alkoxy (such as lower alkoxy, e.g. methoxy), haloalkoxy (such as halo lower alkoxy, e.g. $OCHF_2$ and OCF$_3$), nitro, amino, alkylthio (such as lower alkylthio, e.g. methylthio), —COOH, —CONHSO$_2$R$^5$, —CONH$_2$, —CONHR$^5$, —CONHOR$^7$ (where R$^7$ is lower alkyl such as methyl), —COOCH(R$^4$)COOR$^3$, —NHSO$_2$R$^7$, —N(SO$_2$R$^7$), —SCH(R$^4$)COR$^3$ or —NHCH(R$^4$)COR$^3$.

In each aspect of the invention it is often preferable that any alkyl, alkenyl, alkynyl or alkylene moiety (such as the hydrocarbon moiety of an alkoxy or haloalkoxy group) have less than 6 carbon atoms, e.g. 1 to 3 carbon atoms.

Any acidic compound of Formula I may be converted into a salt such as sodium, potassium, calcium, ammonium, magnesium, or mono-, di- or tri(C$_1$ to C$_4$ alkyl)ammonium or sulfonium or sulfoxonium salt which may also be used as an herbicide.

Z, R', R$^3$, R$^4$, R$^5$, and R$^6$ (as well as Ar, R, X and Y) are as described earlier. Ar and R are so chosen that the Methoxy Analog or Propargyloxy Analog (in which Y" is methoxy or propargyloxy instead of the Y" described above) is a herbicide.

In the preferred compounds of this invention, R and Ar (or X and Y) are so chosen that the Methoxy Analog or the Propargyloxy Analog of such preferred compound has marked herbicidal properties, such Analog showing at least 50% kill of at least one of the following plant species when applied under at least one of the following modes at the rate of 0.5 kg/ha, and more preferably showing such 50% kill when applied at the rate of 0.1 kg/ha:

Species: velvetleaf (*Abutilon theophrasti*), green foxtail (*Setaria viridis*); Modes: pre-emergent, post-emergent. Testing for such herbicidal activity may be carried out in the manner described below (under the heading "Herbicidal Activity").

Representative compounds of this invention (including certain intermediates) are listed in Table 1.

The compounds of this invention may be prepared by the use of steps generally described in the literature or in the Examples and discussion below or by the methods analogous or similar thereto and within the skill of the art. In Example 1 below, the starting material is the Hydroxy Analog of the compound (which Hydroxy Analog is compound 144 of published International Application WO 85/01939). The Hydroxy Analog is treated to form the nitrophenyl ether, which is then treated (Example 1 Step B and Example 2 Step A) to form the hydroxyphenyl ether, followed by etherification with the appropriate moiety. Other methods are illustrated below. In Method B the process is illustrated with a compound in which "M" is N instead of CH; in that method the hydroxypyridyl ether is produced by treating the methoxypyridyl ether or by treating a nitropyridyl ether. In Method C the first step is an etherification to introduce the Q group followed by a reduction of the nitro substituent (on the Ar group) to form an amino group which is then converted to a chlorine substituent. Methods D and E relate to processes for making the Y'—Ar—NH$_2$ compound whose NH$_2$ group can then be converted to the final triazolinone moiety in a conventional manner. In Method D the NH$_2$ group has been acylated to protect it during the various reactions. In Method E that NH$_2$ group is introduced by nitration followed by reduction. While these methods are illustrated specifically with reagents chosen to form the product of Example 1 (or, in Method B, the corresponding pyridyl compound), it will be understood by those skilled in the art that analogous reactants may be used to form other compounds disclosed herein.

Method B: React the Hydroxy Analog, e.g. 1-(4-chloro-2-fluoro-5-hydroxyphenyl)-1,4-dihydro-4-(3-fluoropropyl)-5H-tetrazol-5-one, first with sodium hydride (e.g. in N,N-dimethylformamide ["DMF"] followed by reaction with an appropriately substituted 5-methoxypyridine (e.g. 2-fluoro- or 2-chloro-5-methoxypyridine) to form 1-[4-chloro-2-fluoro-5-(5-methoxypyridin-2-yl)oxyphenyl]-1,4-dihydro-4-(3-fluoropropyl)-5H-tetrazol-5-one. Then treat with boron tribromide (e.g. in methlene chloride) to form the hydroxyether. Alternatively, react the Hydroxy Analog with an appropriately substituted 5-nitropyridine (e.g. 2-fluoro- or 2-chloro-5-nitropyridine) to form 1-[4-chloro-2-fluoro-5-(5-nitropyridin-2-yl)oxyphenyl]-1,4-dihydro-4-(3-fluoropropyl)-5H-tetrazol-5-one, then (in conventional manner) reduce the NO$_2$ group to NH$_2$ and convert the NH$_2$ to OH (as by conventional diazotisation to form the hydroxyether. The hydroxyether may then be reacted with an alkyl (e.g. ethyl) 2-bromopropionate (e.g. in the presence of potassium carbonate and acetone) to form the corresponding alkyl 2-[5-[2-chloro-4-fluoro-5-(1,4-dihydro-5-oxo-4-(3-fluoropropyl)tetrazol-1-yl)phenoxy]-pyridin-2-yl]oxy-propionate.

Method C: React 1-(2,5-difluoro-4-nitrophenyl)-1,4-dihydro-4-(3-fluoropropyl)-5H-tetrazol-5-one with an alkyl (e.g. ethyl) 2-(4-hydroxyphenoxy)propionate in the presence of a base such as sodium hydride in N,N-dimethylformamide to form the alky 2-[4-[4-fluoro-2-nitro-5-(1,4-dihydro-5-oxo-4-(3-fluoropropyl)tetrazol-1-yl)phenoxy]-phenoxy]propionate. Reduce the nitro group by hydrogenation (e.g. in ethanol with a catalytic amount of platinum oxide) to form the alkyl 2-[4-[2-amino-4-fluoro-5-(1,4-dihydro-5-oxo-4-(3-fluoropropyl)tetrazol-1-yl)phenoxy]-phenoxy]propionate. Then treat (as with sodium nitrite and hydrochloric acid, followed by copper (I) chloride) to form the corresponding alkyl 2-[2-chloro-4-fluoro-5-(1,4-dihydro-5-oxo-4-(3-fluoropropyl)tetrazol-1-yl)phenoxy]phenoxy]-propionate.

Method D: React 4-chloro-2-fluoro-5-hydroxyacetanilide with 4-fluoronitrobenzene (e.g. by heating in the presence of a base, such as sodium hydride, and DMF) to form 4-chloro-2-fluoro-5-(4-nitrophenoxy)acetanilide. Reduce the NO$_2$ group (as by hydrogenation in ethanol with a catalytic amount of platinum oxide) to form 5-(4-aminophenoxy)-4-chloro-2-fluoroacetanilide. Treat the latter (e.g. with sodium nitrite and sulfuric acid followed by copper (II) sulfate) to form 4-chloro-2-fluoro-5-(4-hydroxyphenoxy)acetanilide. Then react with an alkyl halide, such as methyl iodide (e.g. in the presence of potassium carbonate and acetone) to form the alkyl 4-chloro-2-fluoro-5-(4-methoxyphenoxy)acetanilide. Hydrolyze the latter (as with hydrochloric acid) to form the corresponding aniline, e.g. 4-chloro-2-fluoro-5-(4-methoxyphenoxy)aniline.

Method E: React 2,5-difluoronitrobenzene with 4-methoxyphenol (e.g. in the presence of a base, such as sodium hydride, and DMF) to form 5-fluoro-2-(4-methoxyphenoxy)nitrobenzene. Reduce the nitro group (as by hydrogenation in ethanol with a catalytic amount of platinum oxide) to form 5-fluoro-2-(4-methoxyphenoxy)aniline. Nitrate the latter (as with nitric acid and sulfuric acid) to form 5-fluoro-2-(4-methoxyphenoxy)-4-nitroaniline. Treat the latter (e.g. first with sodium nitrite and hydrochloric acid followed by copper (I) chloride) to form 4-chloro-2-fluoro-5-(4-methoxyphenoxy)nitrobenzene. Reduce the nitro group (e.g. by hydrogenating in ethanol with a catalytic amount of platinum oxide) to form the corresponding 4-chloro-2-fluoro-5-(4-methoxyphenoxy)aniline.

It will be understood that substituents present in the final product may be introduced at various stages. For instance in methods D and E the methoxy group may be converted to a Q group such as a $C_2H_5O$—CO—CH(CH$_3$)—O— group at a subsequent stage in the process, or the latter group may be introduced earlier, as by using ethyl 2-bromopropionate in place of the methyl iodide in Method D or by using ethyl 2-(4-hydroxyphenoxy)propionate in place of the 4-methoxyphenol in Method E.

EXAMPLE 1

1-(4-Chloro-2-Fluoro-5-Phenoxyphenyl)-1,4-Dihydro-4-(3-Fluoropropyl)-5H-Tetrazol-5-One

Step A

1-[4-Chloro-2-fluoro-5-(4-nitrohenoxy)phenyl]-1,4-dihydro-4-(3-fluoropropyl)-5H-tetrazol-5-one A solution of 9.3 g (0.032 mole) of 1-(4-chloro-2-fluoro-5-hydroxyphenyl)-1,4-dihydro-4-(3-fluoropropyl)-5H-tetrazol-5-one in approximately 30 ml of N,N-dimethylformamide was added to a stirred mixture of 1.5 g (0.030 mole) of sodium hydride (50% suspension in oil) in 100 ml of N,N-dimethylformamide. The mixture was stirred for 15 minutes and 4.50 g (0.0304 mole) of 4-fluoronitrobenzene was added. This mixture was stirred at room temperature for approximately 18 hours then was heated at 80° C. for five hours. The mixture was cooled, poured into ice water and was extracted with ethyl acetate. The extract was dried over anhydrous magnesium sulfate and filtered. The filtrate was evaporated under reduced pressure to leave a solid residue. This residue was purified by recrystallization from n-heptane to yield 8.1 g of 1-[4-chloro-2-fluoro-5-(4-nitrophenoxy)phenyl]-1,4-dihydro-4-(3-fluoropropyl)-5H-tetrazol-5-one, m.p. 109°–110° C.

Step B

1-[5-(4-Aminophenoxy)-4-chloro-2-fluorophenyl]-1,4-dihydro-4-(3-fluoropropyl)-5H-tetrazol-5-one Hydrogenation of 8.0 g (0.0194 mole) of 1-[4-chloro-2-fluoro-5-(4-nitrophenoxy)phenyl]-1,4-dihydro-4-(3-fluoropropyl)-5H-tetrazol-5-one in 220 ml of ethanol and a catalytic amount (0.5 g) of platinum oxide yielded 5.1 g of 1-[5-(4-aminophenoxy)-4-chloro-2-fluorophenyl]-4,5-dihydro-4-(3-fluoropropyl)-5H-tetrazol-5-one as an oil.

Step C 1-(4-Chloro-2-fluoro-5-phenoxyphenyl)-1,4-dihydro-4-(3-fluoropropyl)-5H-tetrazol-5-one To a stirred solution of 4.0 g (0.011 mole of 1-[5-(4-aminophenoxy)-4-chloro-2-fluorophenyl]-4,5-dihydro-4-(3-fluoropropyl)-5H-tetrazol-5-one and 7 ml of concentrated sulfuric acid in 13 ml of water was added 10 g of ice. A solution of 0.93 g (0.013 mole) of sodium nitrite in 10 ml of ice cold water was added dropwise. After complete addition the mixture was allowed to stir at approximately −5° C. for 20 minutes. Small amounts of urea were added until no decomposition of excess sodium nitrite was observed. A solution containing 38.4 g (0.165 mole) of cupric nitrate hemipentahydrate in 60 ml of water was added slowly to the mixture while maintaining a temperature of 0° C. This mixture was stirred for 20 minutes then was extracted first with diethyl ether followed by ethyl acetate. The extracts were combined and dried over anhydrous magnesium sulfate. The dried extract was filtered and the filtrate was evaporated under reduced pressure to leave a liquid residue. Purification of this residue by column chromatography on silica gel, eluted with methylene chloride, yielded 1.3 g of 1-(4-chloro-2-fluoro-5-phenoxyphenyl)-1,4-dihydro-4-(3-fluoropropyl)-5H-tetrazol-5-one as an oil.

EXAMPLE 2

Ethyl 2-[4-[2-Chloro-4-Fluoro-5-[4-(3-Fluoropropyl)-1,4-Dihydro-5-Oxotetrazol-1-yl]Phenoxy]Phenoxy]Propionate

Step A

1-[4-Chloro-2-fluoro-5-(4-hydroxyphenoxy)phenyl]-1,4-dihydro-4-(3-fluoropropyl)-5H-tetrazol-5-one While maintaining a temperature of 5° C. to 10° C., 1.03 g (0.015 mole) of sodiuM nitrite dissolved in 10 ml of water was added to a stirred mixture of 4.76 g (0.0125 mole) of 1-[5-(4-aminophenoxy)-4-chloro-2-fluorophenyl]-1,4-dihydro-4-(3-fluoropropyl)-5H-tetrazol-5-one (prepared by the method of Steps A and B of Example 1 in 6 ml of concentrated sulfuric acid. The resultant mixture was stirred at 6° C. for 30 minutes. This mixture was added to a refluxing mixture of 37.5 g (0.150-mole) of copper II sulfate in 70 ml of xylene/toluene (50/50) and 100 ml of water. After complete addition, the mixture was stirred and heated at reflux for one hour. The mixture was cooled to room temperature and the phases were allowed to separate. The organic phase was extracted with an aqueous sodium hydroxide solution (6.0 g of sodium hydroxide in 250 ml of water). The basic extract was acidified with concentrated hydrochloric acid forming a precipitate. This mixture was extracted with ethyl acetate. The extract was dried over anhydrous magnesium sulfate and filtered. The filtrate was evaporated under reduced pressure to yield 1.35 g of 1-[4-chloro-2-fluoro-5-(4-hydroxyphenoxy)phenyl]-1,4-dihydro-4-(3-fluoropropyl)-5H-tetrazol-5-one as a solid, m.p. 157°–159° C., compound 3 of Table 1.

The nmr and ir spectra were consistent with the proposed structure.

Step B Ethyl 2-[4-[2-chloro-4-fluoro-5-[4-(3-fluoropropyl)-1,4-dihydro-5-oxotetrazol-1-yl]phenoxy]phenoxy]propionate A stirred mixture of 1.0 g (0.0026 mole) of 1-[4-chloro-2-fluoro-5-(4-hydroxyphenoxy)phenyl]-1,4-dihydro-4-(3-fluoropropyl)-5H-tetrazol-5-one, 1.5 g (0.0083 mole) of ethyl 2-bromopropionate, and 0.64 g (0.0046 mole) of potassium carbonate in 50 ml of acetone was heated at reflux for approximately 18 hours. The mixture was cooled and the solvent was removed by evaporation under reduced pressure leaving a residue. This residue was purified by column chromatography on silica gel, eluting with methylene chloride to yield 0.5 g of ethyl 2-[4-[2-chloro-4-fluoro-5-[4-(3-fluoropropyl)-1,4-dihydro-5-oxotetrazol-1-yl]phenoxy]phenoxy]propionate as an oil, compound 8 of Table 1.

The nmr spectrum was consistent with the proposed structure.

The herbicidal data in the following Tables 3 and 4 was obtained in the manner described in PCT published application no. WO 85/01939, published 5/9/85, usually employing solutions of the herbicidal compound in 50/50 acetone/water mixtures. In those tables, the test compounds are identified by numbers which correspond to those in Table 1, "kg/ha" is kilograms per hectare, and "% C" is percent control.

For herbicidal application, the active compounds are formulated into herbicidal compositions by admixture in herbicidally effective amounts with adjuvants and carriers normally employed in the art for facilitating the dispersion of activ ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules (e.g. for paddy rice) in the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Other wettable power formulations are:

| Component: | % by Wt. |
|---|---|
| Active ingredient | 40.00 |
| Sodium ligninsulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium ligninsulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate | |
| 2% powdered sodium lignosulfonate | |
| 2% powdered anionic sodium alkyl-naphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component: | % by Wt |
|---|---|
| Active ingredient | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 41.42 |
| Propylene glycol | 7.50 |
| Acetylenic alcohols | 2.50 |

| Component: | | % by Wt. |
|---|---|---|
| Xanthan gum | | 0.80 |
| | Total | 100.00 |
| Active ingredient | | 45.00 |
| Water | | 48.50 |
| Purified smectite clay | | 2.00 |
| Xanthan gum | | 0.50 |
| Sodium alkylnaphthalenesulfonate | | 1.00 |
| Acetylenic alcohols | | 3.00 |
| | Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acids esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions:

| | | % by Wt. |
|---|---|---|
| Oil Suspension: | | |
| Active ingredient | | 25.00 |
| polyoxyethylene sorbitol hexaoleate | | 5.00 |
| Highly aliphatic hydrocarbon oil | | 70.00 |
| | Total | 100.00 |
| Aqueous Suspension: | | |
| Active ingredient | | 40.00 |
| Polyacrylic acid thickener | | 0.30 |
| Dodecylphenol polyethylene glycol ether | | 0.50 |
| Disodium phosphate | | 1.00 |
| Monosodium phosphate | | 0.50 |
| Polyvinyl alcohol | | 1.00 |
| Water | | 56.70 |
| | Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for preparation of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient inthe range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed, for instance in the greenhouse post-emergent treatment employing compound No. 9 of Table 1 below, rates of application as low as about 8 to 15 g/ha have given effective control of broadleaf weeds with selectivity favorable to rice and wheat and (to a lesser extent) corn. For field application of herbicides it is usual practice to employ higher rates than are effective in the greenhouse, owing to various losses in the field.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl)-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (betazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]amino-2-methylpropanenitrile (cyanazine); dinitrolanilide herbicides such as 2,6-dinitro-N,N-dipropyl-4-(trifluoromethyl)-benzeneamine (trifluoralin); and aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-osoxazolidone.

It is apparent that various modifications may be made in the formulation and application of the compounds of this invention without departing from the inventive concepts herein as defined in the claims.

TABLE 1

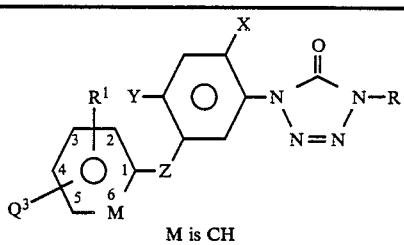

M is CH

| Cmpd. No. | X | Y | Z | R¹ | Q³ | Position of Q³ | R |
|---|---|---|---|---|---|---|---|
| 1 | F | Cl | O | H | H | 4 | (CH₂)₂CH₂F |
| 2 | F | Cl | O | H | NH₂ | 4 | (CH₂)₂CH₂F |
| 3 | F | Cl | O | H | OH | 4 | (CH₂)₂CH₂F |
| 4 | F | Br | O | H | NO₂ | 4 | (CH₂)₂CH₂F |
| 5 | F | Br | O | H | OCH(CH₃)CONHSO₂CH₃ | 4 | (CH₂)₂CH₂F |
| 6 | F | Br | O | H | NH₂ | 4 | (CH₂)₂CH₂F |
| 7 | F | Br | O | H | OCH(CH₃)CO₂C₂H₅ | 4 | (CH₂)₂CH₂F |
| 8 | F | Cl | O | H | OCH(CH₃)CO₂C₂H₅ | 4 | (CH₂)₂CH₂F |
| 9 | F | Cl | O | H | OCH(CH₃)CO₂CH(CH₃)₂ | 4 | (CH₂)₂CH₂F |
| 10 | F | Cl | O | H | NO₂ | 4 | (CH₂)₂CH₂F |
| 11 | Cl | Cl | O | H | OCH₂CO₂CH₃ | 4 | CH₂CH₂F |
| 12 | Cl | Cl | O | H | OCH₂CO₂C₂H₅ | 4 | CH₂CH₂CH₂F |
| 13 | Cl | Cl | O | H | OCH₂CO₂CH(CH₃)₂ | 4 | CH₂CH₂CH₂F |
| 14 | Cl | Cl | O | H | OCH(CH₃)CO₂CH₃ | 4 | CH₂CH₂CH₂F |
| 15 | Cl | Cl | O | H | OCH(CH₃)CO₂H | 4 | CH₂CH₂CH₂F |
| 16 | Cl | Cl | O | H | OCH(CH₃)CO₂C₂H₅ | 4 | CH₂CH₂CH₂F |
| 17 | Cl | Cl | O | H | OCH₂CN | 4 | CH₂CH₂CH₂F |
| 18 | Cl | Cl | O | H | OCH(CH₃)CN | 4 | CH₂CH₂CH₂F |
| 19 | Cl | Cl | O | H | OCH(CH₃)CONH₂ | 4 | CH₂CH₂CH₂F |
| 20 | Cl | Cl | O | H | OCH(CH₃)CONHSO₂CH₃ | 4 | CH₂CH₂CH₂F |
| 21 | Cl | Cl | O | H | OCH(CH₃)CO₂CH(CH₃)₂ | 4 | CH₂CH₂CH₂F |
| 22 | Cl | Cl | O | H | OCH(CH₃)CO₂Na | 4 | CH₂CH₂CH₂F |
| 23 | Cl | Cl | O | H | OCH(CH₃)CO₂CH₃ | 3 | CH₂CH₂CH₂F |
| 24 | Cl | Cl | O | H | OCH(CH₃)CO₂H | 3 | CH₂CH₂CH₂F |
| 25 | Cl | Cl | O | H | OCH(CH₃)CO₂C₂H₅ | 3 | CH₂CH₂CH₂F |
| 26 | Cl | Cl | O | H | OCH(CH₃)CONH₂ | 3 | CH₂CH₂CH₂F |
| 27 | Cl | Cl | O | H | OCH(CH₃)CONHSO₂CH₃ | 3 | CH₂CH₂CH₂F |
| 28 | Cl | Cl | O | H | OCH₂CO₂Et* | 3 | CH₂CH₂CH₂F |
| 29 | Cl | Cl | O | 2-Cl | OCH(CH₃)CO₂Et | 4 | CH₂CH₂CH₂F |
| 30 | Cl | Cl | O | 4-Cl | OCH(CH₃)CO₂Et | 3 | CH₂CH₂CH₂F |
| 31 | Cl | Cl | O | 2-F | OCH(CH₃)CO₂Et | 4 | CH₂CH₂CH₂F |
| 32 | Cl | Cl | O | 4-F | OCH(CH₃)CO₂Et | 3 | CH₂CH₂CH₂F |
| 33 | Cl | Cl | O | 4-NO₂ | OCH(CH₃)CO₂Et | 3 | CH₂CH₂CH₂F |
| 33 | Cl | Cl | O | 4-OCH₃ | OCH(CH₃)CO₂Et | 3 | CH₂CH₂CH₂F |
| 35 | F | Cl | O | H | OCH(CH₃)CONH₂ | 4 | CH₂CH₂CH₂F |
| 36 | F | Cl | O | H | OCH(CH₃)CONHCH₃ | 4 | CH₂CH₂CH₂F |
| 37 | F | Cl | O | H | OCH(CH₃)CON(CH₃)₂ | 4 | CH₂CH₂CH₂F |
| 38 | F | Cl | O | H | OCH(CH₃)CONHC₂H₅ | 4 | CH₂CH₂CH₂F |
| 39 | F | Cl | O | H | OCH₂CO₂C₂H₅ | 4 | CH₂CH₂CH₂F |
| 40 | F | Cl | O | H | OCH₂CO₂CH₃ | 4 | CH₂CH₂CH₂F |
| 42 | F | Cl | O | H | OCH(CH₃)CONC₂H₅SO₂CH₃ | 4 | CH₂CH₂CH₂F |
| 43 | F | Cl | O | H | OCH(CH₃)CONHSO₂CF₃ | 4 | CH₂CH₂CH₂F |
| 44 | F | Cl | O | H | OCH(CH₃)CONCH₃SO₂CF₃ | 4 | CH₂CH₂CH₂F |
| 45 | F | Cl | O | H | OCH(CH₃)CONHSO₂C₆H₅ | 4 | CH₂CH₂CH₂F |
| 46 | F | Cl | O | H | OCH(CH₃)CONHSO₂(4ClC₆H₄) | 4 | CH₂CH₂CH₂F |
| 47 | F | Cl | O | H | OCH₂CN | 4 | CH₂CH₂CH₂F |
| 48 | F | Cl | O | H | OCH(CH₃)CN | 4 | CH₂CH₂CH₂F |
| 49 | F | Cl | O | H | OCH₂COCH₃ | 4 | CH₂CH₂CH₂F |
| 50 | F | Cl | O | H | OCH(CH₃)COCH₃ | 4 | CH₂CH₂CH₂F |
| 51 | F | Cl | O | H | OCH(CH₃)CO₂C(CH₃)C≡CH | 4 | CH₂CH₂CH₂F |
| 52 | F | Cl | O | H | OCH₂C(=NOCH₃)CH₃ | 4 | CH₂CH₂CH₂F |
| 53 | F | Br | O | H | OCH₂CO₂Et | 4 | CH₂CH₂CH₂F |
| 54 | F | Br | O | H | OCH(CH₃)CO₂Et | 4 | CH₂CH₂CH₂F |
| 55 | F | Br | O | H | OCH(CH₃)CO₂H | 4 | CH₂CH₂CH₂F |
| 56 | F | Br | O | H | OCH(CH₃)CO₂CH₃ | 4 | CH₂CH₂CH₂F |
| 57 | F | Br | O | H | OCH(CH₃)CONHSO₂CH₃ | 4 | CH₂CH₂CH₂F |
| 58 | F | Cl | O | H | OC(CH₃)CO₂Et | 4 | CH₃ |
| 59 | F | Cl | O | H | OC(CH₃)CO₂Et | 4 | C₂H₅ |
| 60 | F | Cl | O | H | OC(CH₃)CO₂Et | 4 | C₃H₇ |
| 61 | F | Cl | O | H | OC(CH₃)CO₂Et | 4 | CH(CH₃)₂ |
| 62 | F | Cl | O | H | OC(CH₃)CO₂Et | 4 | CH₂CH=CH₂ |
| 63 | F | Cl | O | H | OC(CH₃)CO₂Et | 4 | CH₂CH₂CF₂H |
| 64 | F | CH₃ | O | H | OC(CH₃)CO₂Et | 4 | CH₂CH₂CH₂F |
| 65 | F | H | O | H | OC(CH₃)CO₂Et | 4 | CH₂CH₂CH₂F |
| 66 | F | NO₂ | O | H | OC(CH₃)CO₂Et | 4 | CH₂CH₂CH₂F |
| 67 | F | OCHF₂ | O | H | OC(CH₃)CO₂Et | 4 | CH₂CH₂CH₂F |
| 68 | F | CF₃ | O | H | OC(CH₃)CO₂Et | 4 | CH₂CH₂CH₂F |
| 69 | F | F | O | H | OC(CH₃)CO₂Et | 4 | CH₂CH₂CH₂F |

TABLE 1-continued

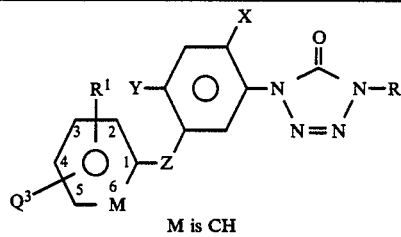

M is CH

| Cmpd. No. | X | Y | Z | R¹ | Q³ | Position of Q³ | R |
|---|---|---|---|---|---|---|---|
| 70 | F | SCH₃ | O | H | OC(CH₃)CO₂Et | 4 | CH₂CH₂CH₂F |
| 71 | F | Cl | O | H | OCH(CH₃)CO₂C₂H₅ | 3 | CH₂CH₂CH₂F |
| 72 | F | Cl | O | H | OCH(CH₃)CO₂H | 3 | CH₂CH₂CH₂F |
| 73 | F | Cl | O | H | OCH(CH₃)CONH₂ | 3 | CH₂CH₂CH₂F |
| 74 | F | Cl | O | H | OCH(CH₃)CONHSO₂CH₃ | 3 | CH₂CH₂CH₂F |
| 75 | F | Cl | O | H | OCH(CH₃)CONHC₆H₅ | 3 | CH₂CH₂CH₂F |
| 76 | F | Cl | O | H | OCH(CH₃)CN | 3 | CH₂CH₂CH₂F |
| 77 | CH₃ | Cl | O | H | OCH(CH₃)CO₂C₂H₅ | 4 | CH₂CH₂CH₂F |
| 78 | Br | Cl | O | H | OCH(CH₃)CO₂C₂H₅ | 4 | CH₂CH₂CH₂F |
| 79 | H | Cl | O | H | OCH(CH₃)CO₂C₂H₅ | 4 | CH₂CH₂CH₂F |
| 80 | F | Cl | O | 2-Cl | OCH(CH₃)CO₂C₂H₅ | 4 | CH₂CH₂CH₂F |
| 81 | F | Cl | O | 4-Cl | OCH(CH₃)CO₂C₂H₅ | 3 | CH₂CH₂CH₂F |
| 82 | F | Cl | O | 2-F | OCH(CH₃)CO₂C₂H₅ | 4 | CH₂CH₂CH₂F |
| 83 | F | Cl | O | 4-F | OCH(CH₃)CO₂C₂H₅ | 3 | CH₂CH₂CH₂F |
| 84 | F | Cl | O | 4-NO₂ | OCH(CH₃)CO₂C₂H₅ | 3 | CH₂CH₂CH₂F |
| 85 | F | Cl | O | 4-Br | OCH(CH₃)CO₂C₂H₅ | 3 | CH₂CH₂CH₂F |
| 86 | F | Cl | O | H | OCH(CH₃)CO₂Na | 4 | CH₂CH₂CH₂F |
| 87 | F | Cl | O | H | OCH(CH₃)CO₂(NEt)₄ | 4 | CH₂CH₂CH₂F |
| 88 | F | Cl | O | H | OCH(CH₃)CO₂K | 4 | CH₂CH₂CH₂F |

*"Et" = C₂H₅

Other representative compounds are identical with each of the foregoing compounds except that in each case M is nitrogen atom.

TABLE 2

| Cmpd No. | Melting Point (°) | Empirical Formula | Elemental Analysis | | | |
|---|---|---|---|---|---|---|
| | | | | C | H | N |
| 1 | oil | C₁₆H₁₃ClF₂N₄O₂ | C | 52.39 | 3.57 | 15.27 |
| | | | F | 52.15 | 3.44 | 14.82 |
| 2 | oil | C₁₆H₁₄ClF₂N₅O₂ | | | | |
| 3 | 157–159 | C₁₆H₁₃ClF₂N₄O₃ | | | | |
| 4 | 114–117 | C₁₆H₁₂BrF₂N₅O₄ | | | | |
| 5 | oil | C₂₀H₂₀BrF₂N₅O₆S | C | 41.67 | 3.50 | 12.15 |
| | | | F | 41.02 | 3.87 | 10.02 |
| 6 | oil | C₁₆H₁₄BrF₂N₅O₂ | | | | |
| 7 | 86–87 | C₂₁H₂₁BrF₂N₄O₅ | C | 47.83 | 4.01 | 10.63 |
| | | | F | 46.79 | 3.53 | 11.08 |
| 8 | oil | C₂₁H₂₁ClF₂N₄O₅ | C | 52.23 | 4.38 | 11.60 |
| | | | F | 50.14 | 4.19 | 11.30 |
| 9 | oil | C₂₂H₂₃ClF₂N₄O₅ | C | 53.17 | 4.67 | 11.28 |
| | | | F | 53.10 | 4.62 | 11.05 |
| 10 | 109–110 | C₁₆H₁₂ClF₂N₅O₄ | | | | |

TABLE 3

Pre-emergence Percent Control

| Compound No. | 1 | 2 | 3 | 4 | 5 |
|---|---|---|---|---|---|
| Rate (kg/ha) | 2.0 | 2.0 | 2.0 | 2.0 | 0.125 |
| Species | | | | | |
| Cotton | 30 | 0 | 10 | 5 | 0 |
| Soybean | 10 | 5 | 40 | 5 | 10 |
| Field Corn | 10 | 0 | 50 | 0 | 5 |
| Rice | 60 | 30 | 20 | 5 | 5 |
| Wheat | 20 | 30 | 50 | 10 | 5 |
| Morningglory | 20 | 10 | 10 | 10 | 0 |
| Wild Mustard | 100 | 0 | 70 | 10 | 60 |
| Velvetleaf | 100 | 70 | 100 | 0 | 10 |
| Barnyardgrass | 95 | 20 | 90 | 10 | 20 |
| Green Foxtail | 100 | 70 | 60 | 40 | 40 |
| Johnsongrass | 95 | 10 | 40 | 20 | 10 |
| Compound No. | 6 | 7 | 8 | 9 | 10 |

TABLE 3-continued

Pre-emergence Percent Control

| Rate (kg/ha) | 2.0 | 0.125 | 0.125 | 0.25 | 2.0 |
|---|---|---|---|---|---|
| Species | | | | | |
| Cotton | 0 | 0 | 0 | 40 | 5 |
| Soybean | 10 | 10 | 0 | 5 | 0 |
| Field Corn | 0 | 0 | 0 | 10 | 0 |
| Rice | 30 | 10 | 5 | 40 | 0 |
| Wheat | 5 | 20 | 10 | 5 | 10 |
| Morningglory | 20 | 50 | 10 | 50 | 5 |
| Wild Mustard | 10 | 80 | 20 | 100 | 10 |
| Velvetleaf | 30 | 80 | 0 | 100 | 10 |
| Barnyardgrass | 30 | 10 | 0 | 30 | 10 |
| Green Foxtail | 60 | 10 | 0 | 100 | 0 |
| Johnsongrass | 40 | 0 | 0 | 30 | 0 |

TABLE 4

Post-emergence Percent Control

| Compound No. | 1 | 2 | 3 | 4 | 5 |
|---|---|---|---|---|---|
| Rate (kg/ha) | 2.0 | 2.0 | 2.0 | 2.0 | 0.125 |
| Species | | | | | |
| Cotton | 100 | 100 | 100 | 80 | 70 |
| Soybean | 60 | 50 | 60 | 20 | 50 |
| Field Corn | 80 | 60 | 40 | 20 | 70 |
| Rice | 40 | 30 | 40 | 10 | 40 |
| Wheat | 40 | 30 | 20 | 30 | 70 |
| Morningglory | 100 | 90 | 50 | 20 | 70 |
| Wild Mustard | 100 | 100 | 60 | 20 | 100 |
| Velvetleaf | 100 | 100 | 100 | 70 | 100 |
| Barnyardgrass | 90 | 30 | 20 | 10 | 30 |
| Green Foxtail | 95 | 90 | 20 | 10 | 40 |
| Johnsongrass | 90 | 40 | 30 | 20 | 50 |
| Compound No. | 6 | 7 | 8 | 9 | 10 |
| Rate (kg/ha) | 2.0 | 0.125 | 0.125 | 0.25 | 2.0 |
| Species | | | | | |
| Cotton | 100 | 100 | 100 | 100 | 30 |
| Soybean | 40 | 60 | 90 | 70 | 20 |
| Field Corn | 70 | 100 | 90 | 100 | 30 |
| Rice | 20 | 40 | 20 | 20 | 40 |
| Wheat | 40 | 70 | 30 | 5 | 20 |

TABLE 4-continued

| | Post-emergence Percent Control | | | | |
|---|---|---|---|---|---|
| Morningglory | 70 | 100 | 100 | 100 | 20 |
| Wild Mustard | 50 | 100 | 100 | 100 | 10 |
| Velvetleaf | 100 | 100 | 100 | 100 | 100 |
| Barnyardgrass | 40 | 80 | 80 | 60 | 10 |
| Green Foxtail | 50 | 100 | 100 | 60 | 40 |
| Johnsongrass | 50 | 100 | 100 | 50 | 10 |

I claim:

1. Compound of the formula:

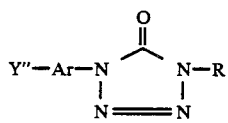

where

Y'''—Ar— is a substituted phenyl radical in which Y" is at the 5-position relative to the nitrogen atom to which Ar is attached;

Y" is

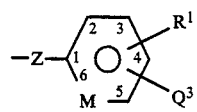

M is CH,

Z is O, S, NH or alkylamino;

$Q^3$ is $-[O-CH(R^{4a})CO]_m-OCH(R^4)Q^2$, $Q^2$ is $-C(O)R^3$ or $-CN$;

$R^4$ and $R^{4a}$ are each independently H, $CH_3$ or $C_2H_5$;

$R^3$ is OH, alkoxy, alkylthio, lower alkenyloxy or alkynyloxy, amino, arylamino, alkylamino, alkenylamino, alkynylamino, alkoxyamino or alkyl-, haloalkyl- or arylsulfonylamino of the formula $-NHSO_2R^5$ or $-N(SO_2R^5)SO_2R^6$, or an $-O-N=R^8$ radical where $R^8$ is alkylidene;

$R^5$ and $R^6$ are each independently alkyl, haloalkyl or aryl;

"m" is zero or one;

$R^1$ is H, alkyl, halogen, haloalkyl, nitro, $NH_2$, lower alkoxy or alkylthio or cyano;

Ar is a substituted benzene ring with Ar and R being so chosen that when Y" is methoxy or propargyloxy, instead of having the formula given above, the compound is a herbicide.

2. The compound of claim 1 in which m is zero, Z is O and Ar is a benzene ring having halogens at its 2- and 4-positions and $Q^2$ is $-C(O)R^3$.

3. The compound of claim 3 in which $R^3$ is lower alkoxy.

4. The compound of claim 3 in which R is 3-fluoropropyl and $R^4$ is $CH_3$.

5. The compound of claim 3 in which Ar has F or Cl at its 2-position and Cl or Br at its 4-position.

6. The compound of claim 5 in which Ar has F at its 2-position.

7. The compound of claim 6 in which Ar is

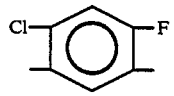

and R is 3-fluoropropyl.

8. An herbicidal composition comprising an herbicidally effective amount of the compound of claim 1 in admixture with a suitable carrier.

9. A method for controlling undesired plant growth which comprises applying to the locus where control is desired an herbicidally effective amount of the composition of claim 8.

10. An herbicidal composition comprising an herbicidally effective amount of the compound of claim 5 in admixture with a suitable carrier.

11. A method for controlling undesired plant growth which comprises applying to the locus where control is desired an herbicidally effective amount of the composition of claim 8.

12. An herbicidal composition comprising an herbicidally effective amount of the compound of claim 7 in admixture with a suitable carrier.

13. A method for controlling undesired plant growth which comprises applying to the locus where control is desired an herbicidally effective amount of the composition of claim 12.

* * * * *